United States Patent [19]

Saint-Remy et al.

[11] Patent Number: 5,026,545
[45] Date of Patent: Jun. 25, 1991

[54] TREATMENT OF ALLERGY AND COMPOSITION THEREFOR

[75] Inventors: Jean-Marie Saint-Remy, Grez-Doiceau; Philippe Lebrun, Namur; Serge Lebeque; Pierre L. Masson, both of Brussels, all of Belgium

[73] Assignees: Baxter International, Inc., Deerfield, Ill.; International Institute of Cellular and Molecular Pathology, Brussels, Belgium

[21] Appl. No.: 410,021

[22] Filed: Sep. 20, 1989

Related U.S. Application Data

[63] Continuation-in-part of Ser. No. 651,073, Sep. 17, 1984, Pat. No. 4,740,371.

[51] Int. Cl.$^5$ ..................... A61K 39/395; A61K 39/35
[52] U.S. Cl. ..................................... 424/85.8; 424/88; 424/91; 424/85.91; 530/389; 530/390; 530/391; 514/826; 514/829; 514/890
[58] Field of Search ......................... 424/85.8, 88, 91; 530/389-391; 514/826, 829, 890

[56] References Cited

U.S. PATENT DOCUMENTS

| | | | |
|---|---|---|---|
| 4,140,679 | 2/1979 | Malley | 424/88 |
| 4,234,569 | 11/1980 | Marsh . | |
| 4,344,938 | 8/1982 | Sedlacek et al. | 530/388 |
| 4,545,986 | 10/1985 | Malley | 424/91 |
| 4,564,600 | 1/1986 | Ali et al. | 436/513 |
| 4,714,759 | 12/1987 | Whitaker | 530/391 |

FOREIGN PATENT DOCUMENTS 0209229 12/1982 Japan ..................................... 424/88

OTHER PUBLICATIONS

Fox, *Nature*, 314, 1985, pp. 132-133.
Gene Cloning; 1984, ed Glover, pp. 102-104.
Principles of Gene Manipulation, 1981, ed. Old et al, pp. 104-105, 119-120.
"Immunoregulation by Antigen/Antibody Complexes", Michael J. Caulfield et al., pp. 3680-3683, *The Journal of Immunology*, vol. 138, No. 11, Jun. 1, 1987.
"The Antibody Response to Specific Immune Complexes is Under Genetic Control and Correlates with the Expression of a Recurrent Idiotype", Michael J. Caulfield et al.. pp. 75-86, *J. Exp. Med.*, vol. 163, Jan. 1986.
"Idiotype-Restricted Antibody Response to Specific Immune Complexes", Michael J. Caulfield, pp. 451-457, *Cellular Immunology* 90, 1985.
"Suppression of Reaginic Antibody Formation", Weng Y. Lee, et al., pp. 829-836, *The Journal of Immunology*, vol. 114, No. 2, Feb. 1975.
"Suppression of Reaging Antibody Formation", Weng Y. Lee, et al., pp. 837-842, *The Journal of Immunology*, vol. 114, No. 2, part 2, Feb. 1975.
"Tolerization of B$_6$ Cells by Conjugates of Haptens and Isologous-Globulins", Weng Y. Lee, et al., pp. 385-397, *Cellular Immunology* 58, 1981.
"Suppression of the IgE Antibody Response to Ovalbumin in Mice with a Conjugate of Ovalbumin and Isologus-Globulins", L. G. Filion, et al., pp. 115-128, *Cellular Immunology* 54, 1980.
"Suppression of Reaginic Antibody Formation", Weng Y. Lee, et al., pp. 927-934, *The Journal of Immunology*, vol. 117, No. 3, Sep. 1976.
"Experimental Myasthenia Gravis Inhibited by Receptor-Antireceptor Complexes", T. Barkas, et al., pp. 223-227, *J. Clin. Lab. Immunol.*, 1982.
"Regulatory Effect of Antibody on the Immune Response", Jonathan W. Uhr, et al., pp. 80-126.
Sanders, "Allergy-A Protective Mechanism Out of Control", 48 C & EN 84-135 (May 1970).
Arend, "In Vitro Adherence of Soluble Immune Complexes to Macrophages", 136 J. Exp. Med. 514 (1972).
Geczy et al, "Suppression of Reaginic Antibody Formation in Guinea Pigs by Anti-Idiotypic Antibodies", 62 J. All. Clin. Immun. 261 (1978).
Klaus, "Antigen-Antibody Complexes Elicit Anti-Idiotypic Antibodies to Self Idiotopes", 272 Nature 265 (1978).
Klaus, "Generation of Memory Cells. III. Antibody Class Requirements for the Generation of B-Memory Cells by . . . ", 37 Immunology 345 (1979).
Klaus, "Cooperation Between Antigen-Reactive T Cells and Anti-Idiotypic B Cells in the Anti-Idiotypic Response . . . ", 278 Nature 354 (Mar. 22, 1979).
Blaser et al, "Suppression of Phosphorylcholine-Specific IgE Antibody Formation in BALB/c Mice . . . ", 9 Eur. J. Immunol. 1017 (1979).
Blaser et al, "Suppression of the Benzylpenicilloyl-(BPO) Specific IgE Formation with Isologous Anti-Idiotypic . . . ", 125 J. Immun. 24 (1980).
Blaser et al, "Investigation of a Syngeneic Murine Model for the Study of IgE Antibody Regulation with . . . ", 64 Inf. Archs Allergy 42 (1981).
Geha, "Current Concepts in Immunology-Regulation of Immune Response by Idiotypic-Antiidiotypic Interactions", 305 New England J. Med. 25 (1981).

(List continued on next page.)

*Primary Examiner*—Garnette D. Draper
*Attorney, Agent, or Firm*—Lane, Aitken & McCann

[57] ABSTRACT

A pharmaceutical composition comprises an immune complex of an allergen and a purified antibody specific thereto, the allergen being selected from a specific subclass of antigen which causes immediate hypersensitivity that is mediated by IgE antibody, and a pharmacologically acceptable carrier or diluent. The method of using the compositions in the treatment of immediate hypersensitivity to the allergen is also described.

26 Claims, No Drawings

OTHER PUBLICATIONS

"Primer on Allergic and Immunologic Diseases", 248 JAMA 2583, Nov. 26, 1982.

Blaser et al, "Regulation of the IgE Antibody Response by Idiotype-Anti-Idiotype Network", 32 Prog. Allergy 203 (1982).

Farkas, "Immunogenicity of Antigen Complexed with Antibody . . . ", 45 Immuno 483 (1982).

Geha et al, "The Regulation of Immunoglobulin E Antibody Synthesis in Man by Anti-Idiotypic Antibodies", 71 J. Clin. Invest. 46 (Jan. 1983).

Caulfield et al, "Induction of Idiotype-Specific Suppression T Cells with Antigen/Antibody Complexes", 157 J. Exp. Med. 1713 (1983).

Blaser et al, "Immune Networks in Immediate Type Allergic Diseases", 418 Ann. NY Acad. Sci. 330 (1983).

Blaser et al, "Regulatory Effects of Isologous Anti-Idiotypic Antibodies on the Formation of . . . ", 14 Eur. J. Immunol. 93-98 (1984).

Buisseret, "Allergy" Scientific American 82-91 (Aug. 1982).

50 Fed. Reg. 3082 (Jan. 23, 1985).

TREATMENT OF ALLERGY AND COMPOSITION THEREFOR

This is a continuation-in-part of U.S. application Ser. No. 651,073, filed Sept. 17, 1984, now U.S. Pat. No. 4,740,371.

BACKGROUND OF THE INVENTION

This invention relates to a method of treating allergy, particularly immediate hypersensitivity, and to pharmaceutical compositions useful therefor.

Immediate hypersensitivity, that is, anaphylactic response, is a form of allergic reaction which develops very quickly, i.e., within seconds or minutes of exposure of the patient to the causative allergen and which is mediated by IgE antibodies made by B lymphocytes. There is very little IgE in non-allergic patients, but in a person suffering from allergy, the concentration of IgE is very much higher. This elevated amount of IgE mediates immediate hypersensitivity by priming mast cells which are abundant in the skin, lymphoid organs, membranes of the eye, nose and mouth, and respiratory tree and intestines. Mast cells have surface IgE receptors, and the elevated concentrations of IgE in allergy-suffering patients become bound to them. When this bound IgE is subsequently contacted by the appropriate allergen, the mast cell is caused to degranulate and release various substances such as histamine into the surrounding tissue. It is the release of these substances which is responsible for the clinical symptoms typical of immediate hypersensitivity, namely, contraction of smooth muscle in the airways or the intestine, the dilation of small blood vessels and increase in their permeability to water and plasma proteins, secretion of thick, sticky mucus and, in the skin, the stimulation of nerve endings that results in itching or pain.

Immediate hypersensitivity is, at best, a nuisance to the sufferer. At worst it can present very serious problems and can in rare, extreme cases result in death. Efforts have been made for many years to find some way of effectively treating sufferers, and essentially three such ways have been found. These are: avoidance of the allergen, desensitization and the use of drugs. Of these, avoidance of the allergen is in one sense clearly the best approach, but of course, it is in practice very difficult, and usually impossible, to achieve. Treatment by the use of drugs is useful, but it is generally directed to alleviating the symptoms of allergy rather than dealing with its causes. Also, there are disadvantages in the use of certain drugs, and it is by no means always possible with drugs to assist patients to the extent desired.

The third method of treatment, namely, desensitization, has long been recognized as perhaps the most hopeful practical approach to the problem. It has been known for over 60 years that the injection into a patient of initially small but subsequently increasing amounts of the offending allergen itself, over a period of time, can often result in an improved resistance to that allergen. This procedure is known as "desensitization" or "allergen immunotherapy". While it is not useful in the treatment of food allergies, it is useful in the treatment of, for example, inhalant allergen-derived sensitivity and allergic reactions due to insect stings.

Curiously, although desensitization has been successfully practiced for many years, the mechanism by which it works is still not known. In most patients, the injection of the allergen appears to give rise, not to IgE antibodies, but rather to IgG antibodies which, upon inhalation by the patient of the allergen in question, combine with the allergen to block its ability to bind to the mast cell IgE. These IgG antibodies are called "blocking antibodies". However, this hypothesis does not always fit the facts. In some patients who are successfully desensitized, there is little specific IgG in their blood, and in other patients for whom the injections have apparently been ineffective against allergy, there is a large amount of the particular IgG.

Whatever the mechanism may be, it remains the fact that many though not all sufferers of immediate hypersensitivity can be helped considerably by desensitization. The technique involves injecting the allergen to which the patient has become sensitized into the patient over a relatively long period of time, e.g., one year or more. Initially, the doses used are very small, but in the absence of contra-indications, they are increased rapidly to high levels which are necessary if the treatment is to be effective.

There are certain problems in desensitization treatment. First, it is necessary for the patient to have injections very frequently, e.g., initially every two or three days, gradually reducing to once every two or three weeks. This is not only a time-consuming procedure, but is also disruptive of the patient's normal routine, and generally undesirable. Also, the dose of allergen administered has to be carefully monitored and controlled, which adds to the complexity of the procedure. A second problem is that, in the treatment itself, there is an element of risk to the patient. Even though initial doses of the allergen are very small and precautions are routinely taken to watch for any allergic response, local or systemic allergic reactions such as hives, asthma and fainting do sometimes occur and can cause death in exceptional cases. For these and other reasons, many practicing physicians are skeptical of desensitization techniques.

Attempts have been made in the past to overcome or avoid these problems. To reduce the frequency of injection, preparations have been administered which release the allergen slowly over a period of time. These have not been very successful for a number of reasons, an important one of which being that, once administered, no control can be exercised over the amount of allergen released into the patient's blood. Another way in which the frequency of injection might be reduced would be to devise a treatment whereby the necessary large doses of allergen are administered rather earlier to the patient, but to date there has been no such treatment devised. Attention is also being directed to the possibility of administering modified allergens instead of the "pure" material itself. Thus, attempts have been made to modify an allergen chemically so that, while its immunogenicity, i.e., its ability to cause an immune response in the patient, is unchanged, its allergenicity is substantially reduced. Success has been achieved with this approach, but it has certain disadvantages of its own. First, each allergen, and there are of course a vast number of allergens against which patients can become sensitized and thus need desensitization treatment, has to be modified individually in accordance with its particular chemical structure, such that there is no satisfactory, universally applicable technique for modifying allergens for a desensitization treatment. Second, a very considerable amount of work can be involved in devising an acceptable modified allergen, bearing in mind the requirements for it to be useful in the desensitization treatment, including the necessity for the chemical modification itself not to cause any adverse reaction in the patient. Third, because accurate control of dose is so important in a desensitization treatment, there can be problems with modified allergens in determining the proper dose required.

Further background information on allergy and desensitization treatments may be found in Paul D. Buiseret, "Allergy", *Scientific American*, August 1982, pp. 82-91; Howard J. Sanders, "Allergy: A Protective Mechanism Out of Control", *C & E News*, vol 48, pp. 84-134 (1970); and "Primer on Allergic and Immunologic Disease", *Journal of the American Medical Association*, volume 248, no. 20 (Nov. 26, 1982).

SUMMARY OF THE INVENTION

The present invention involves a desensitization method for treating immediate hypersensitivity, whereby many of the problems and disadvantages of prior known procedures are reduced or even overcome. In particular, the invention involves a way of administering allergens which is universally applicable to all allergens, which in the preferred embodiment does not expose the patient to any increased risk, and by which large doses of allergen are suitably administered.

In accordance with the present invention, human or animal patients having immediate hypersensitivity to an allergen are desensitized by administering to them the said allergen in admixture with antibody directed against the allergen.

The invention further provides a pharmaceutical composition for use in the above method, which composition comprises a mixture of an allergen and antibody specific thereto, in a suitable form for administration, preferably in a sterile injectable form.

It is to be understood that, in the context of the present invention, the term "allergen" means a specific subclass of antigen which can trigger immediate hypersensitivity, i.e., anaphylactic response, which is mediated by IgE antibody.

DESCRIPTION OF THE PREFERRED EMBODIMENTS

We have found that, by mixing the allergen with an antibody thereto, a number of advantages are achieved over prior art procedures. First, this is a universally applicable and relatively simple way of treating an immediate hypersensitivity. Antibody is raised to any and every allergen, and the mere admixture thereof with the allergen is a straightforward procedure. Second, when the antibody is derived from the patient, the risk of any adverse reaction thereto is virtually eliminated. This is in sharp contrast to prior art procedures for chemically modifying allergens, where adverse reactions are sometimes obtained. Indeed, where an allergen is modified by coupling it chemically to another material, the patient can become sensitized to the other material. This does not occur with the use of naturally occurring antibody. In alternative embodiments, the antibody is derived from pooled human gammaglobulins or monoclonal antibodies.

The clinical efficacy of the present invention is very good. Patients who have failed to respond to prior art desensitization techniques have been found to benefit from treatment with the present invention. The duration of treatment of the present invention is in certain embodiments markedly less than in prior known procedures. Further, it is usually possible in accordance with the present invention to reach much higher allergen doses more quickly than in prior known procedures, although this is not necessary in order for the clinician to administer large quantities to initiate an efficient response. Also, the treatment of the invention does not appear to generate any significant local or systemic allergic reaction, and thus the risks in its use are less than those using prior art modified allergens.

The mechanism by which the treatment method of the invention works is not known. It is hypothesized that the mixture of allergen and antibody inevitably contains allergen:antibody immune complex, and that the antibody thus masks the allergenicity of the allergen. This would explain the very much reduced allergenicity of the complex. The reason why the method of the invention can achieve such a marked desensitization is not understood, and indeed any such explanation may have to wait for a better understanding of the mechanism of desensitization generally. It is surprising that mixtures of allergens and antibodies thereto are so effective as desensitizing agents, in that there is no apparent reason why they should be. Regardless, the scope of the ensuing claims is not intended to be limited in any way by a specific actual or hypothesized mechanism of action.

It is not uncommon for patients who suffer anaphylactic response to a particular allergen, also to suffer such a response to one or more other allergens. However, it is possible by the method of the invention to desensitize such a patient in respect of two or more allergens simultaneously, by administering the said allergens in admixture with antibodies against each allergen. Thus, in one embodiment, a composition of the invention comprises a mixture of two allergens and two families of antibodies, each family directed against a respective allergen. Alternatively, simultaneous desensitization in respect of two or more allergens can be effected by administering two or more compositions of the invention, each composition comprising one allergen only and its respective antibodies.

We have referred above to the compositions of the invention comprising antibodies against the allergen. It should be understood that, instead of whole antibody, antibody fragment such as F(ab')$_2$ is used in an alternative embodiment. In a still further embodiment, monoclonal antibodies are used.

In practicing the present invention, there are essentially three steps, namely:

(1) Identification of the allergen and preparation of the antibody thereto;

(2) Formation of the mixture of allergen and antibody to make a composition of the invention; and (3) Administration of the composition to the patient.

These steps will now be described in more detail.

1. Identification of the Allergen and Preparation of the Antibody

The allergen responsible for an allergy can be determined by standard known techniques. An antibody thereto is then generated. Three sources of antibody can be used: (a) immunized animals, (b) individual blood donors and pooled plasma from multiple donors, and (c) the patient himself. It is preferred to use antibodies from the patient because the patient will normally have larger amounts of the specific antibodies required than will blood donors. On the other hand, the use of antibodies from pooled plasma is commercially desirable since it allows the preparation of pre-packaged allergen-antibody complexes without involving the patient. Antibodies of animal origin are generally the least desirable to use because of the risk of undesirable side reactions.

The antibody is suitably polyclonal or monoclonal and is used, for example, in a purified state or in the form of an immunoglobulin fraction. Purification of the antibody has the advantage of removing therapeutically irrelevant materials. The use of polyclonal antibodies decreases the risk of allergenic reactions against unmasked antigenic determinants.

The antibody is suitably purified by various known techniques such as, for example, specific absorption on the allergen which has been insolubilized by coupling to a solid phase. The antibody is then recovered by elution under conditions which dissociate the allergen-antibody complex, such as conditions of extreme pH, or by the use of chaotropic agents.

2. Formation of the Composition of the Invention

Compositions of the invention are made by mixing the allergen or allergens with the antibody or antibodies, in a form suited to the particular mode of administration that is selected. Because the antibody will react only with its specific allergen, almost any preparation of allergen, even in the form of crude extracts, is suitably used, provided it is devoid of toxic substances. However, the use of pure or relatively pure preparations of allergen is preferred because it is then easier to assess and control the amount of allergen present, which is important in controlling doses.

In other embodiments, the allergen is chemically modified by gluteraldehyde, ethylene glycol derivatives or the like. In still other embodiments, the allergen is an antigenic determinant produced by genetic engineering, or the allergen is mimicked by monoclonal antibodies.

The proportion of antibody to be added to the allergen is defined essentially by the neutralizing power of the antibody. The ratio of allergen to antibody depends largely on the size of the allergen, since the number of antigenic determinants on the allergen is in general proportional to the molecular weight of the allergen. Enough antibody must be used so that, when the composition is administered, there is practically no allergic effect by the allergen. The minimum amount of antibody is normally a molar equivalent of allergen, and the antibody is preferably present in a molar excess relative to the amount of allergen. If desired, routine testing reveals for any particular allergen and antibody, the minimum amount of antibody to be used. There is no maximum to the amount of antibody which is used. For safety, a molar excess of up to about 500 is used. An even larger antibody excess can be utilized but it is, of course, wasteful of the valuable material. A suitable dosage range for the allergen is from about 1 ng to about 100 $\mu$g. The strength of the compositions is preferably expressed in terms of the allergen concentration and the allergen to antibody ratio. The selection of suitable ratios of allergen to antibody and allergen dosages is illustrated in the foregoing examples.

One simple method of preparing the mixture of allergen and antibody, which avoids the necessity of purifying the allergen or the antibody, is the use of the immune precipitate. In one embodiment, the precipitate is prepared by incubating a crude preparation of immunoglobulin from the patient's plasma or serum with the allergen, and then centrifuging. The precipitation process is enhanced by the addition of polymers such as polyethylene glycol and dextran, or biological reagents such as rheumatoid factor or the Clq factor of complement. These techniques are well known.

The compositions of the invention contain, in addition to the allergen and antibody, any other suitable components. For example, in the case of injectables, suitable additional components include human albumin to prevent denaturation of antibody, antiseptic agents such as phenol and the like, and adjuvants such as peptidoglycans, tyrosine crystals and the like.

Suitable liquid carriers for the composition when in injectable form include distilled water, or more preferably saline or buffered saline. In preferred embodiments, a saline carrier of 9 grams per liter of sodium chloride is used, or a buffered saline carrier having a pH of 7.4. In general, suitable liquid carriers are of low irritance, e.g., of neutral pH and physiological ionic strength. The selection of other pharmacologically acceptable carriers and diluents for use in the compositions is within the skill of those ordinarily skilled in the art.

The compositions of the invention are prepared in a variety of forms depending on the manner of administration. Thus, they are suitably prepared in a sterile injectable form, slow-release implant form, a form suitable for local application to nasal, bronchial, lacrimal and/or gastrointestinal mucosae, in which case they are suitably in an aerosol or spray form or in a form similar to eye or nose drops, or as protected enteric capsules or the like. Other suitable forms will be readily apparent to those ordinarily skilled in the art.

When the compositions are prepared in liquid form, the liquids are suitably solutions or suspensions. The liquids are suitably stored in ampoules or are lyophilized and reconstituted immediately prior to use. The compositions of the invention are fairly stable and, in sterile ampoules, can normally be stored at 4° C. for a limited time, or at −20° C. for 12 to 24 months. When lyophilized, their storage life is much longer.

3. Administration of the Compositions

The injectable compositions of the invention are suitably injected in various ways: intradermally, subcutaneously, intramuscularly and, with great care, intravenously. The intradermal route is preferred in that it has the advantage of causing a very clear skin reaction if insufficient antibody is present to provide the necessary neutralizing of the allergen in the composition. The frequency of injections varies very widely, for example from daily to yearly, depending upon the type of allergen, the severity of the disease and the stage of desensitization. The dose of allergen is usually doubled at each injection, which is, of course, a very fast increase in dose. Greater or lesser increases are of course suitable depending upon a particular clinical situation.

Compositions of the invention in forms other than injectables are administered in any suitable manner. For example, respiratory allergy is treated by aerosol administration using, for example, a Micronebulizer (Bird) to give particles between 0.5 and 5 um at a rate of 0.35 ml/min, the patient being instructed to breathe in once deeply and to hold his or her breath for two seconds. The dose is repeated at, for example, weekly intervals over the desired period.

The quantity of allergen in the composition used for the first administration, e.g., injection, is suitably equal to and usually much higher, for example, eighty times higher, than those amounts of allergen used in classical desensitization techniques. Thus, in classical techniques, the usual initial dose is from about $10^{-10}$ g to $10^{-9}$ g, for example, from 0.1 to 1 nanogram of purified allergen from the house dust mite is used for the first injection in classical desensitization techniques. In the method of the present invention, a suitable initial dose of allergen is used in an allergen:antibody molar ratio of 1:1 to 1:500, and in the preferred embodiment the amount of antibody exceeds that of allergen, in an allergen:antibody molar ratio of from 1:3 to 1:30. The preferred initial dose, in accordance with the invention, is normally different from one patient to another and corresponds to that dose which causes a skin reaction of 3 to 5 mm diameter after intradermal injection.

It will be readily apparent to those skilled in the art that modifications to the presently described techniques of preparation are suitable in the practice of the present invention and are within the scope of the invention as claimed. For example, a solid phase support for the allergen in alternative embodiments includes membranes and the like.

Comprehensive listings of allergens that can trigger immediate hypersensitivity which is mediated by IgE antibody are set forth in proposed rules of the Federal Food and Drug Administration, reported at *Federal Register*, Vol. 50, No. 15, pages 3082-3288 (Jan. 23, 1985) and in a notice issued by that agency, reported at *Federal Register*, Vol. 50, No. 154, pages 32314-32318 (Aug. 9, 1985). These publications are hereby incorporated by reference. Compositions of the present invention include complexes of the allergens listed in those publications with the corresponding specific antibodies. In order that the invention may be more fully understood, the following examples illustrate the treatment of patients suffering from hypersensitivities to representative allergens.

EXAMPLE 1

Treatment of Patients Suffering from

Allergic Asthma Caused by House Dust Mite (*Dermatophagoides pteronyssinus* or DPT)

1. Patients

The three patients of Example 1 are identified as follows:

| Patient | Initials | Sex | Age |
| --- | --- | --- | --- |
| 1 | L. L. | F | 40 |
| 2 | B. J. | M | 21 |
| 3 | W. E. | F | 37 |

The patients were selected on the following criteria:
1. Long-term (more than 5 years) history of invalidating bronchial asthma, keeping them away from work at least 3 months a year and having necessitated at least one admission in intensive care.
2. Evidence for an extrinsic asthma where DPT was clearly the causative agent.
3. High sensitivity to DPT shown by intradermal testing and bronchial provocation test with the allergen.
4. High level of DPT-specific antibodies.
5. A history of at least one unsuccessful classical desensitization to DPT.
6. No permanent corticotherapy.

All three patients were taking drugs daily. These included theophylline and derivatives, $\beta_2$ agonists in aerosol and topical nasal beclomethasone in one patient (B. J.). They were not suffering from any other known disease, except that two of them (B. J. and W. E.) had a chronic rhinitis. One patient (W. E.) was also highly sensitive to grass pollen as shown by hay fever and asthma during the pollen season and by a high level of specific IgE antibodies against pollens.

The patients were submitted to a 3-month treatment in accordance with the invention, using antigen-antibody complexes made with their own purified antibodies.

2. Antibody Purification a. Plasma collection and handling

One hundred ml of plasma from each patient were precipitated with 18% $Na_2SO_4$ at 37° C. for 4 hours. The precipitate was washed and resuspended in phosphate buffered saline (PBS) containing 1M NaCl and, after centrifugation to clear off small particles, filtered through a 0.45μ filter. Twenty-five ml of this solution were applied onto a 9×90 cm TSK HF-55 (Merck, Darmstadt) gel column, chromatographed at a rate of 250 ml/h and recovered in 10 ml fractions. The two main peaks represented IgM and IgG (plus IgA and IgE). Cross contamination was about 5% as shown by immunodiffusion.

IgM and IgG (plus IgA and IgE) were concentrated separately by ultrafiltration through an XM-100 Amicon membrane to a volume of ~25 ml and dialyzed for 3 days against PBS with several changes of the dialysis bath. The solutions were then passed through a 0.22 μGV filter (Millipore) and stored in sterile conditions.

b. Preparation of the Immunoadsorbent

Commercially available allergens were purified by gel filtration chromatography on Ultrogel AcA 44 and/or Ultrogel AcA 54 (LKB) and, in some cases, by specific immunoadsorption on insolubilized polyclonal or monoclonal specific antibodies.

The allergen was then coupled with carbodiimide to carboxylated agarose (CH-Sepharose 4B; Pharmacia Fine Chemicals). For this purpose, the allergen was incubated at pH 4.5 with 0.1M carbodiimide and carboxylated agarose for 24 hr. at 21° C.

The remaining reactive groups on the solid phase were inactivated by its incubation with 1M glycine for 3 h. at 21° C. The immunoadsorbent was then washed alternatively with 0.1M acetate buffer pH 4.0 and 0.1M carbonate buffer pH 8.3, both containing 0.5M NaCl. To avoid the elution of undesired material with the antibodies of interest, the gel was submitted prior to immunoadsorption to the elution conditions to be described hereafter and to an additional washing with 3M ammonium thiocyanate.

c. Extraction of the Specific Antibodies

The immunoglobulin fractions (1-2 g) from each of the patients were applied onto an immunoadsorbent column (5 ml; 10×2 cm; flow rate 20 ml/h) and the specific antibodies recovered after appropriate washings. Washing was accomplished by:
1. Washing with PBS until the optical density at 280 mm was less than 0.02.
2. Washing with PBS containing 1M NaCl to eliminate non-specific adsorption.
3. Washing with 50 ml of 9 g/l NaCl.
4. Eluting with successive aliquots of 50 ml citric acid, pH 2.7 followed by PBS.

Each new wash and elution step was pursued until no protein was detectable in the effluent. Fractions eluted with citric acid and PBS were pooled immediately, neutralized with dropwise addition of 2M TRIS-HCl buffer, concentrated on a YM 10 ultrafiltration membrane and dialyzed against PBS for 48 h. The eluate was then filtered through a 0.22μ filter and stored at 4° C. in sterile vials. The immunoadsorbent was washed with 3M ammonium thiocyanate for 20 min and finally with 100 ml PBS. All buffers were filtered in 0.22μ filter.

d. Yield and Class Repartition of Specific Antibodies

The amounts of specific antibodies, estimated by optical absorbance of 280 nm, ranged from 2 to 6 mg per 100 ml of plasma.

The analysis of the eluted antibodies failed to reveal the presence of autoantibodies such as rheumatoid factor (anti-IgG autoantibody) and showed that the specific antibodies were of the following classes: IgG (50%), IgM (35%), IgA (14.5%) and IgE (0.5%). No other plasma protein was detected in significant amounts by immunonephelometry.

3. Preparation of Antigen-Antibody Complexes a. Precipitation Curve

To determine the optimal ratio of allergen versus antibody at which most antigenic determinants are hidden by specific antibodies, we made a precipitation curve as follows. Into a series of tubes containing the same amounts of antibodies were pipetted increasing dilutions of allergen in 0.1M borate buffer pH 8.5. Polyethylene glycol was then added to a final concentration of 200 g/l. After incubation for 4 h. at 21° C., then for 16 h. at 4° C. and centrifugation at 8,000 g for 20 min., the precipitates were washed and the amount of protein in the supernatant and the precipitate estimated by the Lowry technique. For safety purposes, we used for the injection 1/5 of the amount of allergen giving the largest precipitate. In these conditions, the antibody was in large excess (allergen to antibody weight ratio=1:500).

b. Preparation of the Complexes and Injectable Compositions

Allergen and antibody were mixed in a weight ratio of 1:500 in 9 g/l NaCl containing 0.3% human serum albumin and 0.4% phenol. All solutions were passed through a sterile 0.22μ filter and handled in sterile conditions. The final volume was 2 ml and contained 400 μg antibody and 800 ng allergen. The injectable solutions were kept in sealed vials at 4° C. until use.

4. Injections

Patients' Tolerances

To assess the patients' tolerances to the compositions, we serially diluted the allergen in the presence of a constant amount of antibodies (the compositions being generally as described in paragraph 3(b) above). Each of these dilutions was then injected intradermally in 20 μl aliquots starting with the lowest allergen-antibody ratio. An interval of 15 minutes was then allowed between the injections. The highest allergen-antibody ratio giving an acceptable skin reaction (wheal of maximum 3 cm diameter) was chosen and used throughout the study. At a ratio of 1:500, the complex usually caused a small skin reaction or none at all.

b. Injection Scheme

Intradermal injections on the internal side of the arm were repeated every week for six weeks, then every fortnight for a total of three months. In a typical scheme, a volume of 20 μl containing 4 μg antibody and 8 ng allergen was used for the first injection. This volume was doubled every week up to a maximum of 200 μl and maintained to the end of the study (a total of 3 months).

5. Clinical Outcome a. Subjective Assessment

No side effects were noted. The patients were reported to feel well and improved as far as their asthmatic symptoms were concerned. No one injection in any of the three patients gave a clear allergic reaction (there were 40 injections in all). At the injection site, there was either a relatively weak skin reaction or none at all.

b. Clinical Assessment

Three criteria were used to evaluate the clinical outcome of the patients: (1) skin reactivity to the allergen, (2) bronchial provocation test with the allergen, and (3) baseline lung function.

1. Skin Reactivity

The allergen was serially diluted in 9 g/l NaCl with 0.3% albumin and 0.4% phenol, and 20 μl was injected intradermally into the arm. After 20 minutes, the wheal area was measured by planimetry and plotted on a graph against the allergen concentration. The amount of allergen needed to obtain a certain wheal area was then read on the curve. The same preparation of allergen was used for the tests made before and after immunotherapy. In the three patients, it was found necessary after treatment to use 16 times more allergen to induce a skin reaction as intense as the one observed before treatment.

2. Bronchial Provocation Test

To assess the bronchial reactivity to DPT before and after immunotherapy, the patients were submitted to aerosols of DPT at different dilutions. Under well standardized conditions, the forced expiratory volume per second ($FEV_1$) and airway conductance were assessed. By plotting the values of these two parameters against the allergen dilution, the dilution of allergen giving a 20% fall in $FEV_1$ or a 35% decrease in airway conductance was determined. Non-specific bronchial reaction to acetylcholine was assessed in this way. Table 1 compares the bronchial sensitivity of patients 1 to 3 before and after three months of immunotherapy.

TABLE 1A

Non-Specific Bronchial Reactivity to Dilute Acetylcholine and Specific Bronchial Reactivity to Dilute DPT Before and After Three Months of Immunotherapy

| Patient | Reactivity to acetylcholine Before | After | Reactivity to DPT Before | After |
|---|---|---|---|---|
| 1. (L. L.) | $10^{-3}$ | ND* | $10^{-3.8}$ | ND |
| 2. (B. J.) | $10^{-2.5}$ | $>10^{-2}$** | $10^{-2.6}$ | $>10^{-1}$** |
| 3. (W. E.) | $10^{-3}$ | $10^{-3.5}$ | $10^{-4}$ | $>10^{-1}$** |

*ND means "not determined".
**No bronchial reactivity observed at the highest concentration of acetylcholine or DPT used.

3. Baseline Lung Function

Baseline $FEV_1$ and airway resistance were assessed during the clinical follow-up. The three patients of Example 1 achieved over 100% of the normal values (111, 127 and 102% respectively for patients 1, 2 and 3) after three to four weeks of treatment. These values were maintained throughout the study except for patient 1 where the $FEV_1$ dropped to 70% of the normal; for this reason no bronchial provocation test was done for this patient.

6. Laboratory Investigations a. Specific Antibodies

Laboratory investigations of DPT-specific antibodies were made before and after 9 weeks of treatment. Results are given in Table 1B.

TABLE 1B

| | DPT-Specific Antibodies Before and After Nine Weeks of Treatment | | | | | |
|---|---|---|---|---|---|---|
| | IgG* | | IgE** | | Total IgE | |
| Patient | Before | After | Before | After | Before | After |
| 1. (L. L.) | 31 | 45 | 16 | 124 | 1,696 | 1,470 |
| 2. (B. J.) | 31 | 34 | 118 | 288 | 2,182 | 2,058 |
| 3. (W. E.) | 27 | 32 | 10 | 42 | 855 | 551 |

*in µg/ml
**in ng/ml

It can be seen from Table 1B that (a) DPT-specific IgG increased moderately, (b) DPT-specific IgE increased dramatically, and (c) total IgE tends to decrease slightly. The same profile was observed for the three patients.

b. IgE Synthesis in Vitro

The total amount of IgE synthesis in vitro was evaluated on peripheral lymphocytes maintained in culture for 7 days. IgE was assayed in the supernatant by radioimmunoassay. The results are shown in Table 1C.

TABLE 1C

| | Total IgE Synthesis | | | | | |
|---|---|---|---|---|---|---|
| | Weeks | | | | | |
| Patient | 1 | 3 | 7 | 11 | 15 | 18 |
| 1. (L. L.) | 1,300* | 850 | 395 | 1,500 | 380 | 7,400 |
| 2. (B. J.) | 1,600 | 810 | 400 | 200 | ND** | <50 |
| 3. (W. E.) | 6,250 | 4,500 | 300 | 350 | ND | <50 |

*in pg/ml supernatant.
**ND means "not determined".

Results indicated in Table 1C show that in vitro production of total IgE tends to decrease in all three patients through the seventh week of the study. These results continue in Patients 2 and 3 through the 18th week. Total IgE levels, however, are influenced by several factors. During the course of the study it was determined that Patient 1 had developed an infectious bronchitis which may account for the increase in the total IgE count.

EXAMPLE 2

Treatment of Pollen Hypersensitive Patient Suffering from Atopic Dermatitis

A 45-year old woman had suffered for more than 10 years from a severe atopic dermatitis with recurrent arm and face skin infections. Classical treatment including oral corticosteroids and restrictive diets had been extensively used without significant benefit. Topical steroids alleviated the pruritis but were of only mild effect on the lesions themselves. Blood analysis showed a normal white cell count and differential, normal renal and liver functions and normal levels of immunoglobulins, apart from a gross elevation of total IgE (10,607 IU/ml) which were found repeatedly. RAST analysis showed a positivity of 4+ for grass pollen.

In April 1985, the patient was treated by weekly intradermal injections of an allergen-antibody mixture made of grass pollen allergens and her own pollen allergen-specific antibodies, prepared according to the process described in Example 1, at a weight ratio of 1:10. The mixture, made of 4 µg antibody and 400 ng allergen, was dissolved in 200 µl of 0.9% saline with 0.3% human albumin and 0.4% phenol. The amount of injected material was increased each time according to the scheme shown in Table 2 for a total of 10 injections.

No systemic or local side effects were observed, either immediate or delayed. After the second injection the skin lesions began to vanish and disappeared almost completely after 3 weeks of treatment. One month after the last injection the lesions reappeared on the arms but were maintained to a very mild degree and without infection for several months. One year later, the patient was submitted to the same treatment. The skin lesions on the arms soon improved and disappeared completely on the face. Pruritis was virtually absent 10 days after the treatment began. The patient is now kept on a maintenance dosage for 6 months in a much improved status.

TABLE 2

| Injection Scheme for Pollen Hypersensitive Patient Suffering from Atopic Dermatitis | | |
|---|---|---|
| Injection | Antibody (µg) | Allergen (ng) |
| 1 | 4 | 400 |
| 2 | 8 | 800 |
| 3 | 16 | 1600 |
| 4 | 24 | 2400 |
| 5 | 32 | 3200 |
| 6 | 40 | 4000 |
| 7 | 50 | 5000 |
| 8 | 60 | 6000 |
| 9 | 70 | 7000 |
| 10 | 80 | 8000 |

EXAMPLE 3

Treatment of Grass Pollen Hypersensitive Patients

Twenty-six patients suffering from vasomotor rhinitis due to pollen hypersensitivity, with in some cases bronchial asthma, urticaria and/or conjunctivitis, were randomly allocated to a treated or placebo group. The treated group was inoculated intradermally on a weekly basis with a mixture of grass pollen allergen and their 20 own purified allergen-specific antibodies prepared as described in Example 1, with a regular increase in the dosage. The details of the injection scheme are listed in Table 3. The placebo group was inoculated with the solvent solution (sterile 0.9% saline containing 0.3% human serum albumin). Both groups were treated from April till the end of July, a period corresponding to the grass pollen season in Belgium. Diary cards monitoring nasal, eye, skin and bronchial symptoms together with medication taken were filled in by the patients throughout the study.

No local or systemic side effects were observed with the exception of a two cm wheal reaction on 3 occasions over a total of 169 injections in the treated group. Clinical and medication scores were significantly improved in the treated group compared to the placebo (Mann-Whitney U test; $p<0.005$ and $p<0.016$ respectively.) Six out of the 13 treated patients did not take medication during the grass pollen season, compared to only 1 in the placebo group (Fisher test; $p<0.036$).

Specific anti-grass pollen IgE showed the expected increase in the placebo group whereas in the treated group specific IgE were maintained at the pre-season level or even decreased during the pollen season (Mann-Whitney U test; $p<0.002$).

TABLE 3

| Pollen Hypersensitive Patient Injection Scheme | | |
|---|---|---|
| Injection | Antibody (ng) | Allergen (ng) |
| 1 | 80 | 8 |
| 2 | 160 | 16 |
| 3 | 320 | 32 |
| 4 | 480 | 48 |
| 5 | 640 | 64 |
| 6 | 800 | 80 |
| 7 | 1000 | 100 |
| 8 | 1200 | 120 |
| 9 | 1600 | 160 |
| 10 | 2000 | 200 |
| 11 | 2400 | 240 |
| 12 | 2800 | 280 |
| 13 | 3200 | 320 |

EXAMPLE 4

Treatment of DPT Hypersensitive Patients

First Dosage Scheme

Twenty-six patients were selected who were hypersensitive to Dermatophagoides pteronyssinus (DPT) and were suffering from severe bronchial asthma, wheezing and shortness of breath, causing occasional interruption of normal activities. For years, these patients took oral corticosteroids for short periods of time in addition to the regular use of theophillyne derivatives, beta-2-agonists and sodium cromoglycate.

Thirteen patients, randomly selected, were treated by fortnightly intradermal injections of a solution containing the allergen with their own purified allergen-specific antibodies. The composition was prepared as described in Example 1. The patients received DPT allergen and their own purified allergen-specific antibodies at a weight ratio of 1:5. The mixture was initially made of 40 ng of antibody and 8 ng of allergen. The amount of injected material was increased according to the injection scheme listed in Table 4 up to the maximal dose of 3200 ng of antibodies and 640 ng of allergen. The treatment, which started in November 1985, lasted one year, with a maintenance dose, made of 3200 ng of antibody and 640 ng of allergen, being since November 1986 injected every six weeks. Thirteen patients served the as control group.

No systemic or side effects were noted. Although the patients of the control group experienced heavy symptoms with the need for corticosteroids intake during the year, the 13 treated patients had significant reduction of their clinical symptoms, reduction in medication intake and no need for corticosteroids.

TABLE 4

| Injection Scheme for DPT Hypersensitive Patients | | |
|---|---|---|
| Injection | Antibody (ng) | Allergen (ng) |
| 1 | 40 | 8 |
| 2 | 80 | 16 |
| 3 | 160 | 32 |
| 4 | 200 | 40 |
| 5 | 400 | 80 |
| 6 | 400 | 80 |
| 7 | 400 | 80 |
| 8 | 800 | 120 |
| 9 | 600 | 160 |
| 10 | 1200 | 240 |
| 11 | 1600 | 320 |
| 12 | 2000 | 400 |
| 13 | 2400 | 480 |
| 14 | 2800 | 560 |
| 15 | 3200 | 640 |
| '' | '' | '' |
| '' | '' | '' |
| 26 | 3200 | 640 |

EXAMPLE 5

Treatment of DPT Hypersensitive Patients

Second Dosage Scheme

Thirteen patients were selected who were hypersensitive to Dermatophagoides pteronyssinus (DPT) and who were suffering from severe bronchial asthma, wheezing and shortness of breath, causing occasional interruption of normal activities. For years, these patients took oral corticosteroids for short periods of time in addition to the regular use of theophillyne derivatives, beta-2-agonists and sodium cromoglycate.

These thirteen patients were treated by fortnightly intradermal injections of a solution containing the allergen with their own purified allergen-specific antibodies. The composition was prepared as described in Example 1. The patients received DPT allergen and their own purified allergen-specific antibodies in a weight ratio of 1:5. The mixture was initially made of 40 ng of antibody and 8 ng of allergen. The amount of injected material was increased according to the injection scheme listed in Table 5 up to the maximal dose of 400 ng of antibodies and 80 ng of allergen. The treatment, which started in November 1985, lasted one year, with a maintenance dose being since November 1986 injected every six (6) weeks, said dose comprising 400 ng of antibody and 80 ng of allergen. The thirteen patients from Example 4 above served as the control group.

No systemic or side effects were noted. Although the patients of the control group experienced heavy symptoms with the need for corticosteroids intake during the year, the 13 treated patients had significant reduction of their clinical symptoms, reduction in medication intake and no need for corticosteroids.

TABLE 5

| Injection Scheme for DPT Hypersensitive Patients | | |
|---|---|---|
| Injection | Antibody (ng) | Allergen (ng) |
| 1 | 40 | 8 |
| 2 | 80 | 16 |
| 3 | 160 | 32 |
| 4 | 200 | 40 |
| 5 | 400 | 80 |
| 6 | 400 | 80 |
| 7 | 400 | 80 |
| '' | '' | '' |
| '' | '' | '' |
| 26 | 400 | 80 |

EXAMPLE 6

Penicillin Hypersensitive Patient Treated with Penicillin-Antibody Complexes

Anaphylactic reactions to medications like penicillin or sulfamides are treated with the present invention.

A patient suffering from allergy to penicillin is treated with the present invention according to the following procedure. Benzyl-penicilloyl (BPO) moities are coupled to a carrier protein, viz. human serum albumin (HSA). The BPO-HSA complex is then coupled to a Sepharose solid phase by a standard cyanogen bromide activation process. Such process is described in "Affinity Chromatography" by M. Wilchek, T. Miron and J. Kohn in *Methods in Enzymology*, Vol. 104, pages 3-55, edited by W. B. Jakoby and published 1984 by Academic Press, Inc.

The patient receives intradermally BPO-coupled human serum albumin and his own penicillin-specific antibodies at a weight ratio of 1:30. The mixture is initially made of 300 ng of antibody and 10 ng of BPO-HSA allergen. The mixture is dissolved in 0.9% saline with 0.3% human serum albumin and 0.4% phenol as preservative. The amount of injected material is increased according to the scheme listed in Table 6 up to a maximum dose of 3000 ng of antibody and 100 ng of allergen per inoculation.

No systemic side effect is noted. At the end of the treatment significant reduction of the hypersensitivity to penicillin is noted.

TABLE 6

| | Penicillin Hypersensitive Patient Injection Scheme | |
|---|---|---|
| Injection | Antibody (ng) | Allergen (ng) |
| 1 | 300 | 10 |
| 2 | 600 | 20 |
| 3 | 1200 | 40 |
| 4 | 1800 | 60 |
| 5 | 2400 | 80 |
| 6 | 3000 | 100 |
| " | " | " |
| " | " | " |
| 15 | 3000 | 100 |

EXAMPLE 7

Treatment of Cat Pelt Hypersensitive Patients

Occupational exposure to agents of vegetable origin (grain, flour, wood dust), animal origin (rat, mouse, locust, fungi), or chemicals (isocyanates, di-isocyanate compounds, epoxy resins, colophony, polyvinyl chloride) sometimes result in the development of asthma, rhinitis and/or urticaria. An IgE-mediated reaction has been demonstrated in some of these conditions and is suspected in others. No treatment is currently available for these situations except avoidance.

A patient suffering from cat pelt allergy is treated with the present invention according to the following procedure. The cat pelt allergens are covalently bound to the solid phase according to the process described in Example 1.

The patient receives intradermally the allergen and his own cat allergen-specific antibodies in a weight ratio of 1:3. The mixture is initially made of 30 ng of antibody and 10 ng of allergen. The mixture is dissolved in 0.9% saline with 0.3% human serum albumin and 0.4% phenol as preservative. The amount of injected material is increased according to the scheme listed in Table 7 up to a maximum dose of 300 ng of antibody and 100 ng of allergen per inoculation.

No systemic side effect is noted. At the end of the treatment significant reduction of the hypersensitivity to cat pelt is noted.

TABLE 7

| | Injection Scheme for Cat Pelt Allergen Hypersensitive Patient | |
|---|---|---|
| Injection | Antibody (ng) | Allergen (ng) |
| 1 | 30 | 10 |
| 2 | 60 | 20 |
| 3 | 120 | 40 |
| 4 | 180 | 60 |
| 5 | 240 | 80 |
| 6 | 300 | 100 |
| " | " | " |
| " | " | " |
| 15 | 300 | 100 |

EXAMPLE 8

Treatment of Honey Bee Venom Hypersensitive Patients

A patient suffering from honey bee venom hypersensitivity is treated with the present invention according to the following procedure. Phospholipase A is covalently bound to a Sepharose solid phase using a standard cyanogen bromide activation process.

The patient receives intradermally a mixture of the allergen and his own honey bee venom allergen-specific antibodies at a weight ratio of 1:10. The mixture is initially made of 50 ng of antibody and 5 ng of allergen. The mixture is dissolved in 0.9% saline with 0.3% human serum albumin and 0.4% phenol as preservative. The amount of injected material is increased according to the scheme listed in Table 8 up to a maximum dose of 500 ng of antibody and 50 ng of allergen per inoculation.

No systemic side effect is noted. At the end of the treatment significant reduction of the hypersensitivity to honey bee venom is noted.

TABLE 8

| | Injection Scheme for Honey Bee Venom Allergen Hypersensitive Patient | |
|---|---|---|
| Injection | Antibody (ng) | Allergen (ng) |
| 1 | 50 | 5 |
| 2 | 100 | 10 |
| 3 | 150 | 15 |
| 4 | 200 | 20 |
| 5 | 250 | 25 |
| 6 | 300 | 30 |
| 7 | 400 | 40 |
| " | " | " |
| 15 | 500 | 50 |

EXAMPLE 9

Treatment of Peanut Allergen Hypersensitive Patient

For food hypersensitivity reactions, and especially peanut allergy, there is currently no efficient therapy.

A patient hypersensitive to peanuts is treated with the present invention according to the following procedure. The peanut allergens are covalently bound to a solid phase using a standard cyanogen bromide activation process. The patient receives intradermally the allergens and his own peanut allergen-specific antibodies at a weight ratio of 1:5. The mixture is initially made of 50 ng of antibody and 10 ng of allergen. The mixture is dissolved in 0.9% saline with 0.3% human serum albumin and 0.4% phenol as preservative. The amount of injected material is increased according to the scheme listed in Table 9 up to a maximum dose of 500 ng of antibody and 100 ng of allergen per inoculation.

No systemic side effect is noted. At the end of the treatment significant reduction of the hypersensitivity to peanuts is noted.

TABLE 9

Injection Scheme for Patients Hypersensitive to Peanut Allergens

| Injection | Antibody (ng) | Allergen (ng) |
|---|---|---|
| 1 | 50 | 10 |
| 2 | 100 | 20 |
| 3 | 200 | 40 |
| 4 | 250 | 50 |
| 5 | 300 | 60 |
| 6 | 400 | 80 |
| 7 | 500 | 100 |
| " | " | " |
| 15 | 500 | 100 |

EXAMPLE 10

Mold Hypersensitive Patient Treated with Immune Complex Encapsulated in an Implantable Slow Release System A patient suffering from allergy to Alternaria tenuis is treated with the present invention according to the following procedure.

Allergens extracted from Alternaria tenuis are covalently bound to a solid phase matrix using a standard cyanogen bromide activation procedure. The patient receives intradermally the allergen and his own Alternaria tenuis allergen-specific antibodies at a weight ratio of 1:20. The mixture is initially made of 400 ng of antibody and 20 ng of allergen. The mixture is dissolved in 1.5 ml of 0.9% saline with 0.3% human serum albumin and 0.1M epsilon amino caproic acid as inhibitor of proteolysis. The mixture is transferred into a slow release implantable system adapted to release the total amount of the mixture within six weeks.

No systemic side effect is noted. At the end of the treatment significant reduction of the hypersensitivity to Alternaria tenuis is noted.

EXAMPLE 11

Honey Bee Venom Hypersensitive Patient Treated by Complexes from Phospholipase A and a Monoclonal Antibody Against Phospholipase A Monoclonal antibodies against phosopholipase A are produced in rodents or, preferably, by fusion of human B lymphocytes from patients hypersensitive to honey bee venom with a human myeloma cell line. The antibody produced in this way is mixed with the allergen to produce a complex suitable for the application of the present invention.

A patient hypersensitive to honey bee venom is treated by regular injections of a complex made from human monoclonal antibody against phospholipase A and phospholipase A in a weight ratio of 4:1. The complex is diluted in 0.9% sodium chloride containing 0.3% human serum albumin and 0.4% phenol as preservative. The initial dose is 1 ng phospholipase A with 4 ng specific antibody. An intradermal injection is made every 20 minutes by doubling the doses each time but keeping the same antibody:antigen ratio. A series of 17 injections is made to reach a maximum dosage of +/− 100 µg phospholipase A. At the end of the treatment the patient is stung by a honey bee under strict medical control, and no signs of hypersensitivity are observed.

EXAMPLE 12

Use of Monoclonal Antibodies as a Source of Allergenic Material in Patients Hypersensitive to Benzyl-Penicillin Monoclonal antibodies are prepared against the allergen-binding site of allergen-specific monoclonal or polyclonal antibodies. These monoclonal antibodies bear on the variable part a structure mimicking the structure of the initial allergen and are used to elicit an immune response against the allergen. A method for preparing monoclonal antibodies is described in "Immunochemical Techniques-Part 1 -Hybridoma Technology and Monoclonal Antibodies" in *Methods in Enzymology*, Vol. 121, edited by J. J. Langone and H. Van Zumakis and published in 1986 by Academic Press, Inc.

A patient hypersensitive to penicillin is treated by regular intradermal injections of autologous specific anti-BPO antibodies as described in Example 6 mixed with a monoclonal antibody mimicking the structure of the BPO hapten. The weight ratio of allergen to antibody is 1:1. The initial dosage is 1 ng of antigen and antibody. The injections are made daily by doubling the dose each time up to a maximum dose of 1 mg of allergen and antibody. No side effects are noted, and at the end of the treatment the patient is able to tolerate pharmacological doses of benzyl-penicillin and derivatives.

EXAMPLE 13

Use of Synthetic and Genetically Engineered Peptides as Allergen in Treatment of DPT Hypersensitivity Most allergens carry a small number of antigenic determinants which are made of a small number of amino acids, usually 3 to 6. These antigenic determinants are synthesized in vitro and used instead of the original antigen. They are usually coupled to a carrier protein with variable degrees of substitution. As an alternative, the antigenic determinants are purified and sequenced and the corresponding DNA sequence determined. This DNA is introduced in the genome of a microorganism which is used to synthesize the allergen in vitro. References teaching suitable genetic engineering techniques include (1) *Molecular Cloning*, by T. Maniatis, E. F. Fritsch, and J. Sambrook, published 1982 by Cold Spring Harbor Laboratory, (2) *Solid Phase Biochemistry*, by B. R. Wallace and K. Itakura, page 631, edited by W. H. Scouten and published 1983 by J. Wiley & Sons, New York, and (3) K. Murray, *Philosophical Transactions of the Royal Society of London-Part B*, Vol. 290, pages 369–386 (1980).

A patient hypersensitive to P1, a major allergen of D.pteronyssinus (see Examples 4 and 5) is treated by regular intradermal injections of autologous anti-P1specific antibodies mixed with a synthetic peptide representative of the antigenic determinants of P1. The peptide was previously coupled to human serum albumin, with a degree of substitution of 5 (an average of 5 peptides per albumin molecule). The weight ratio of allergen to antibody is 1:10. The injections are made weekly, starting at an allergen dosage of 10 ng and followed by two-fold increases of the dosage to reach a dose of 100 μg allergen. After this treatment, no sign of hypersensitivity to P1 is detectable by skin testing or a bronchial provocation test, and the level of specific anti-P1 IgE and IgG is decreased.

EXAMPLE 14

Treatment of Grass Pollen Hypersensitive Patient

This patient was a 39-year old woman with a severe allergic hypersensitization to grass pollens. She had been suffering a severe bronchial asthma, vasomotor rhinitis and recurrent episodes of generalized urticaria, all symptoms which were always confined to the grass pollen season (April to July in Belgium, her country of residence) and related to exposure to the offending allergen. No other allergy had been diagnosed. For about 10 years she had to take oral corticosteroids in addition to the regular use of theophylline derivatives, beta-2-agonists and sodium cromoglycate.

The patient was treated by weekly injections of a solution made by the allergen with her own specific anti-allergen antibodies. The solution was prepared in accordance with the procedure described in Example 1. The treatment started in April and lasted six weeks, and a maintenance dose was then injected fortnightly. No side effects were noted. Although patients allergic to pollen normally experience heavy symptoms during this season, this woman had absolutely no evidence of asthma, rhinitis or urticaria. More impressively, she took no medication through the pollen season. At the end of July she complained of a light rhinitis which was eliminated with an anti-histamine drug.

Having illustrated the practice of the invention in connection with several specific embodiments, those of ordinary skill in the art are taught to vary the elements of the invention, such as allergen dosage, allergen-antibody ratio, carrier, preservative, preparation of allergen-specific antibodies, and manner and periodicity of administration as may be appropriate to treat immediate hypersensitivity that is mediated by IgE antibody. The examples are modified in alternative embodiments by deriving the antibodies from plasma pools, rather than individual patients. The examples are also modified in alternative embodiments by the preparation of various types of insolubilized allergen supports. It will be readily apparent to those skilled in that art that these and other modifications, such as the employment of various types of extraction procedures for the specific antibodies and the use of solubilized allergens, are within the spirit and scope of the present invention.

What is claimed is:

1. A pharmaceutical composition for administration to human beings for the treatment of immediate hypersensitivity to an allergen, said composition consisting essentially of:
   an immune complex of the allergen and a purified antibody specific thereto, said allergen being selected from a specific subclass of antigen that can cause immediate hypersensitivity that is mediated by IgE antibody, said antibody being present in said composition in a molar excess with respect to said allergen present in said composition; and
   a pharmacologically acceptable carrier or diluent.

2. The composition of claim 1, further comprising a mixture of said allergen and said antibody of which said complex is a part, the antibody of said mixture being present in said molar excess with respect to said allergen of said mixture.

3. The composition of claim 1, wherein said antibody of said complex is present in said molar excess with respect to said allergen of said complex.

4. The composition of claim 1, wherein the amount of antibody is such that, when the composition is administered, there is no significant allergenic effect.

5. The composition of claim 1, wherein the allergen to antibody molar ratio is from about 1:3 to about 1:30.

6. The composition of claim 1, wherein the allergen is present in a dose of from about $1.0 \times 10^{-10}$ g to about $8.0 \times 10^{-8}$ g.

7. The composition of claim 1, wherein said composition is in sterile injectable form.

8. The composition of claim 1, wherein said antibody is human-derived.

9. The composition of claim 8, wherein said antibody is derived from a patient suffering immediate hypersensitivity to the allergen.

10. The composition of claim 8, wherein said antibody is derived from pooled plasma from multiple donors.

11. The composition of claim 1, wherein said antibody is a polyclonal antibody.

12. The composition of claim 1, wherein said antibody is a mixture selected from the group consisting of monoclonal antibodies and fractions derived from monoclonal antibodies.

13. The composition of claim 12, wherein said antibody is in the form of $F(ab')_2$ fragments.

14. The composition of claim 1, wherein said antibody consists of a mixture of antibodies selected from isotypes of the group consisting of IgG, IgM, IgA, and IgE.

15. The composition of claim 14, wherein said antibody consists of a mixture of about 50% IgG antibody, about 35% IgM antibody, about 14.5% IgA antibody, and about 0.5% IgE antibody.

16. The composition of claim 1, wherein said composition comprises two or more allergens and two or more respective families of antibodies thereto.

17. The composition of claim 1, wherein said allergen is phospholipase A, and said antibody is a mixture selected from the group consisting of monoclonal antibodies against phospholipase A, and fractions derived from monoclonal antibodies.

18. A desensitization method for reducing the immediate hypersensitivity of a human being to an allergen, said allergen being selected from a specific subclass of antigen that can cause immediate hypersensitivity that is mediated by IgE antibody, said method comprising the steps of administering a composition comprising an immune complex of said allergen and antibody specific thereto to said human being, wherein the molar amount of antibody in said composition exceeds the amount of allergen in said composition such that there is no significant allergic effect by the allergen.

19. The method of claim 18, wherein said mixture is repeatedly administered, whereupon a dosage of allergen is gradually increased.

20. The method of claim 18, further comprising the step of deriving said antibody from a human source.

21. The method of claim 20, further comprising the step of deriving said antibody from said human being.

22. The method of claim 20, further comprising the step of deriving said antibody from a pooled plasma from multiple donors.

23. The method of claim 18, further comprising the step of genetically engineering said allergen.

24. The method of claim 18, further comprising the step of synthetically producing said allergen.

25. The method of claim 18, wherein said allergen is P1, a major allergen of Dermatophagoides pteronyssinus, the method further comprising the step of genetically engineering P1.

26. The method of claim 18, wherein said allergen is P1, a major allergen of Dermatophagoides pteronyssinus, the method further comprising the step of synthetically producing P1.

* * * * *

UNITED STATES PATENT AND TRADEMARK OFFICE
CERTIFICATE OF CORRECTION

PATENT NO. : 5,026,545

DATED : June 25, 1991

INVENTOR(S) : Jean-Marie Saint-Remy et al.

It is certified that error appears in the above-identified patent and that said Letters Patent is hereby corrected as shown below:

Title page, under 'Related U.S. Application Data', Item [63], insert before "Continuation-in-part" the following --Continuation of U.S. Application Serial No. 07/038,985, filed April 16, 1987, now abandoned, which in turn was a --.

In Column 1, line 5, insert before "Continuation-in-part" the following --Continuation of U.S. Application Serial No. 07/038,985, filed April 16, 1987, now abandoned, which in turn was a --.

In Column 12, line 43, delete "20".

Signed and Sealed this

Twenty-eighth Day of September, 1993

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 5,026,545

DATED : June 25, 1991

INVENTOR(S) : Jean-Marie Saint-Remy et al.

It is certified that error appears in the above-indentified patent and that said Letters Patent is hereby corrected as shown below:

On the title page, item [73], delete "Baxter International, Inc., Deerfield, Ill.;"

Signed and Sealed this

Twenty-first Day of March, 1995

Attest:

BRUCE LEHMAN

*Attesting Officer*           *Commissioner of Patents and Trademarks*